United States Patent [19]

McGown et al.

[11] Patent Number: 4,909,090
[45] Date of Patent: Mar. 20, 1990

[54] VAPOR SAMPLING PROBE

[75] Inventors: James B. McGown, Attleboro; Edward E. A. Bromberg, Peabody; Lynn W. Noble, Lexington, all of Mass.

[73] Assignee: Thermedics Inc., Woburn, Mass.

[21] Appl. No.: 341,883

[22] Filed: Apr. 24, 1989

[51] Int. Cl.[4] ............................................. G01N 1/24
[52] U.S. Cl. ............................. 73/864.33; 73/863.12
[58] Field of Search ........... 73/864.33, 863.11, 863.12, 73/863.21, 863.23, 864

[56] References Cited

U.S. PATENT DOCUMENTS 3,067,619 12/1962 Fielding ........................... 73/864.33
3,748,905 7/1973 Fletcher et al. ............. 73/864.33 X

FOREIGN PATENT DOCUMENTS 2088055 6/1982 United Kingdom ............. 73/864.33

OTHER PUBLICATIONS

*Vacuum Probe Sampler Removes Micron-Sized Particles from Surfaces,* In AEC-NASA Tech Brief 68-10231, Jul. 1968.

Spangler, G. E. et al., *Analysis of Explosives and Explosive Residues with Ion Mobility Spectrometry (IMS),* In Proceedings of the International Symposium on the Analysis and Detection of Explosive, Mar. 1983, pp. 267-282.

*Primary Examiner*—Hezron E. Williams
*Assistant Examiner*—Joseph W. Roskos
*Attorney, Agent, or Firm*—Herbert E. Messenger

[57] ABSTRACT

Disclosed is a portable, hand-held vapor sampling probe for collecting vapors of compounds such as cocaine, heroin, and explosives prior to their desorption and analysis in a vapor detector. Rechargable batteries power a lamp in the front face of the probe for heating target portions of a sampling surface, a puffer assembly for directing air jets at the target, and a motor for drawing air samples through a collector coil on whose surfaces vapors are trapped. A flexible U-shaped shroud on the front face partially encloses the lamp and collector and helps to regulate air flow over the target and to protect the probe from damage. Upon contact with a surface, the shroud may activate a switch which, together with a second switch on the probe handle and a lamp pyrometer, regulates heating of the target.

24 Claims, 3 Drawing Sheets

VAPOR SAMPLING PROBE

This invention was made with Government support under Contract No. 2038-563371 awarded by the Department of State. The Government has certain rights in this invention.

BACKGROUND OF THE INVENTION

This invention relates to air sampling and more particularly to an improved hand-operable, portable vapor sampling probe for collecting vapors of specific compounds present in the air or on surfaces.

One method of detecting certain compounds such as explosives involves vapor sampling followed by analysis of the sampled vapors. For example, G. E. Spangler et al. in their paper "Analysis of Explosives and Explosives Residues With Ion Mobility Spectrometry (IMS)" included in the Proceedings of the International Symposium on the Analysis and Detection of Explosives March 29-31, 1983, FBI Academy, Quantico, Virginia, disclose a surface sampler closely coupled to a hand-held ion mobility spectrometer (IMS). The surface sampler includes a conical inlet which may be placed near a surface and in which are mounted a tungsten halogen lamp to heat the surface and air jet nozzles to cause turbulence in the conical inlet. A sample released from the surface swirls up transport lines to the IMS for detection.

Another form of vapor sampling equipment, described in the 1983 paper of D. F. Wardleworth et al. entitled "A Novel Method For the Recovery of Volatile Explosives Traces", is a contact heater including a spring-loaded platen with a hole through which air is drawn by a pump for collection of vapors such as explosives in a Tenax absorbent trap. The contact heater is heated to about 100° C. and kept in contact with a sample surface for 2-5 minutes while vapors are collected. Later the vapors are eluted from the absorbent trap with ethyl acetate and analyzed by gas chromatography or mass spectroscopy.

For maximum effectiveness and versatility a vapor sampler must fulfill several requirements. It should permit acquisition of samples both from surfaces and from open areas (i.e., areas remote from surfaces which may contain the source of such vapors). The vapor sampler should be lightweight, portable, and easy to operate and aim at a specific target. It should collect samples rapidly and without damaging the sampling surface or altering the vapors in a manner which interferes with their analysis. If the collected vapors are to be analyzed in a separate apparatus, the vapor sampler must also facilitate rapid transfer of collected vapors to the vapor analyzer.

Accordingly, it is an object of the invention to provide an improved sampling probe for rapidly collecting vapors of selected compounds such as explosives or the drugs cocaine and heroin.

It is an object of the invention to provide a portable vapor-sampling probe for collecting vapors from surfaces and which controls the flow of air over a target portion of a sampling surface.

An object of the invention is to provide a portable, battery-operable vapor-sampling probe capable of heating a target portion of a sampling surface and preventing overheating of the target.

It is an object of the invention to provide a portable vapor-collecting probe which facilitates rapid transfer of vapors from a collector to a vapor analyzer.

It is a particular object of the invention to provide a portable vapor sampling probe which draws a sample into its collector in a manner such that essentially all air in the sample passes over a heated target portion of the surface.

SUMMARY OF THE INVENTION

The invention is an improved portable, hand-held vapor-sampling probe for collecting vapors of materials such as explosives and the drugs cocaine and heroin. Within a front face of the probe is a collector such as a coil whose windings contain a surface coating effective to trap selected vapors from an air sample drawn through the collector by a blower within the probe. Also mounted in the front face at a location adjacent to the collector are a lamp for heating a target portion of a sampling surface when the probe is positioned near or in contact with the surface and (optionally) a puffer assembly whose air jets help dislodge vapors from the target. The probe may also include a pyrometer with a sensor whose field of view is aligned with that of the lamp so as to measure the temperature of the target. Through its interaction with a control board in the probe, the pyrometer turns off the lamp when necessary to avoid temperatures which could damage the sampling surface or decompose vapors to be collected.

An important feature of the vapor-sampling probe is a flexible shroud on its front face which protects the probe from damage and whose shape helps control the flow of air samples into the collector. A preferred shroud is U-shaped, forming a channel partially enclosing the lamp and the collector, and with the open end of the U closer to the lamp than to the collector. When the probe is positioned with the shroud in contact with a sampling surface and the lamp opposite a target portion to be sampled, activation of the lamp and blower in the probe causes air to be drawn first over the heated target and then through the collector.

The flexible shroud preferably includes, or abuts, a contact switch which may be employed to trigger operation of the lamp and the puffer assembly when pressure is applied to the shroud by contact with a sampling surface. A switch is also provided in a handle of the vapor-sampling probe and is connected to the control board to activate, either alone or in cooperation with the contact switch, the blower lamp, puffer assembly, and pyrometer of the probe.

DETAILED DESCRIPTION OF PREFERRED EMBODIMENTS

Figure 1:
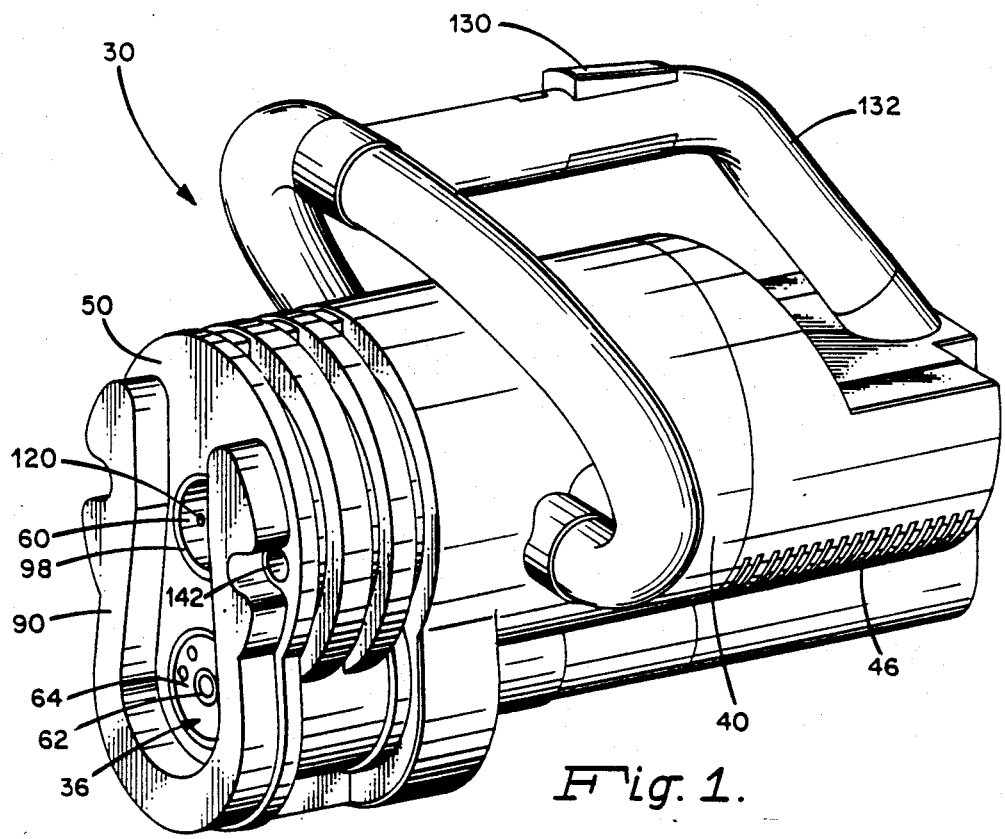
FIG. 1 is a view in perspective of a vapor-sampling probe according to a preferred embodiment of the invention.

A preferred vapor-sampling probe 30 (FIGS. 1–5) according to the invention is a battery-powered, hand-held unit which generates air samples containing vapors and draws the samples through a collector 36 mounted in a collection chamber 38 in the front end of a housing 40. Vapors are trapped on coated surfaces of the collector 36 and the remaining portion of the sample is exhausted through air vents 46 near the rear end of the housing 40. The front end of the probe 30 is configured to mate with and lock to a vapor analyzer (not shown) for subsequent desorption and analysis of vapors.

Unless otherwise specified in this document the term "vapor" is intended to mean a gas, an aerosol, small particles, or any other mobile medium in which specific compounds of interest may be transported in air. Compounds whose vapors are of primary interest are nitrogen-containing hydrocarbons such as the drugs cocaine and heroin and various explosives such as trinitrotoluene (TNT), dinitrotoluene (DNT), ethylene glycol dinitrate (EGDN), pentaerythritol tetranitrate (PETN), nitroglycerin (NG), and others.

The vapor-sampling probe 30 or sample gun is useful in collecting vapors present in the air after the vapors have emanated from a surface or from a place of concealment within a container or the clothing of a person. It is particularly suited for stripping vapors from surfaces which may contain traces of explosives or drugs indicative of larger quantities of those materials concealed nearby and/or from surfaces which have been contacted by persons handling the compounds to be detected.

Figure 3:
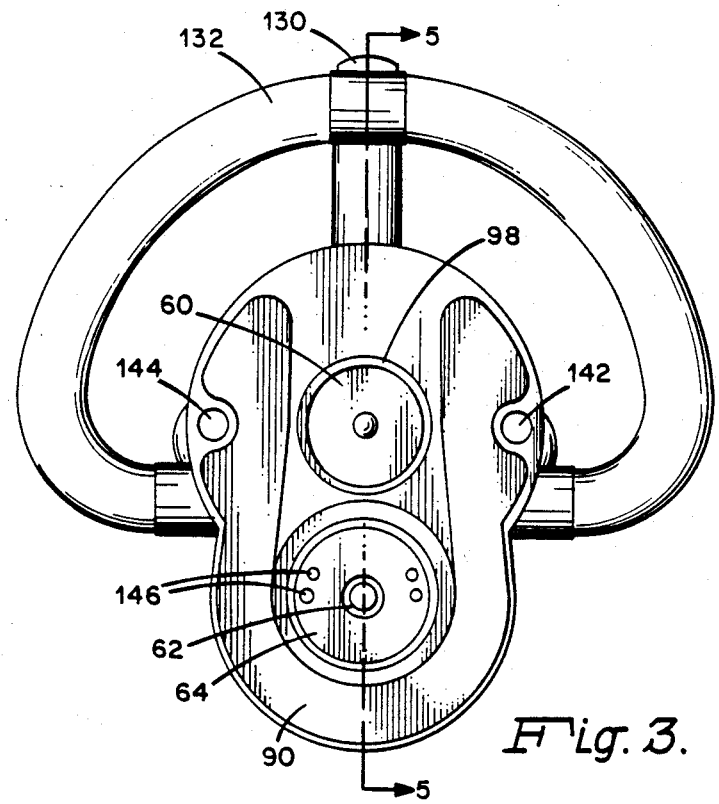
FIG. 3 is a front end view of the vapor-sampling probe of FIG. 1.
Figure 4:
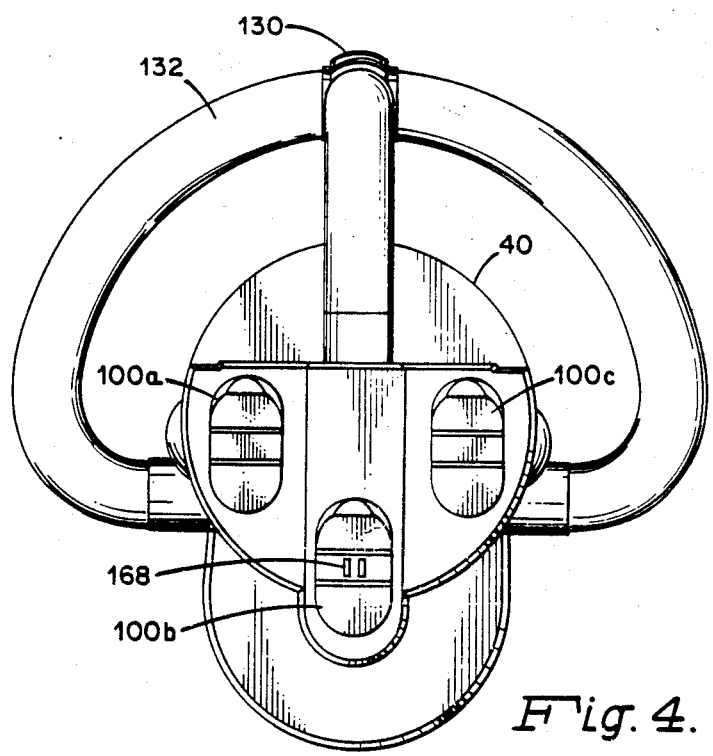
FIG. 4 is a rear end view of the vapor-sampling probe of FIG. 2.
Figure 5:
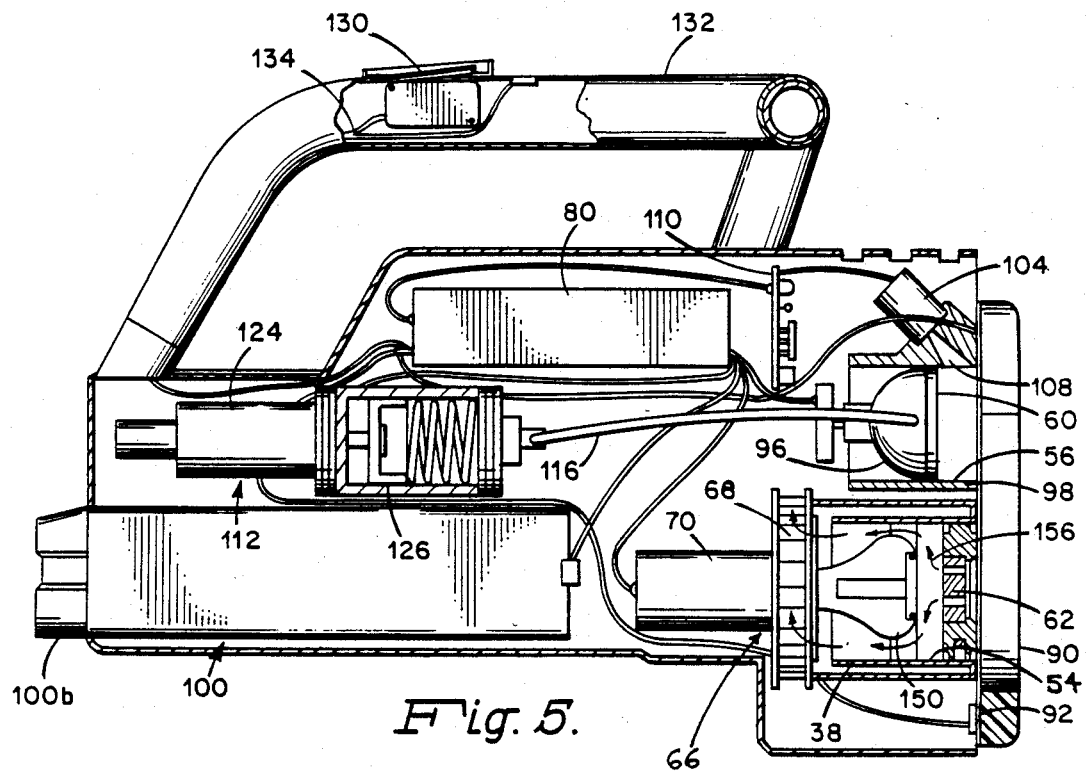
FIG. 5 is a cross-sectional side view of the vapor-sampling probe taken along the line 5—5 of FIG. 3.

The generation and collection of air samples from a surface will now be discussed with reference to particular structural features of the vapor-sampling probe 30. As shown in FIGS. 1, 3, and 4, the front end of the probe housing 40 includes a generally flat front face 50 having two vertically-separated openings 54 and 56 for containing, respectively, the collector 36 and a heater which preferably comprises an electrically-powered lamp 60. The collector 36 typically includes a coil 62 somewhat similar in appearance to an automobile cigarette lighter and which is held in a cylindrical housing 64. The coil contains ribbon-like windings of metal such as molybdenum which have a thin coating of material such as an organic polymer effective to absorb or otherwise to trap the vapors of interest from an air sample directed through the coil 62, and later to release them into a carrier gas upon electrical heating of the metal windings of the coil 62. To draw air samples into the probe 30, a blower 66 is mounted within the housing 40 behind the collection chamber 38 and includes an impellor 68 driven by an electrical motor 70. Air and other constituents of the air sample not trapped on the collector surfaces flow through hollow portions of the housing 40, cooling certain components such as rear portions of the heating lamp 60 and the main electrical control board 80 (FIG. 5). These untrapped portions of the air sample are exhausted through the air vents 46.

An important feature of the vapor-sampling probe 30 is that it controls the speed and direction of air flow into its collector 36. In particular, the probe 30 acquires samples rapidly from specific locations on surfaces, at sufficient air velocities to scrub the "target" area of the surface, and without significant dilution of the air sample. Flow control in the vapor-sampling probe 30 is achieved in part by use of a flexible boot or shroud 90 attached to the front face 50 of the housing 40. The shroud 90, typically formed of a flexible foam material such as silicone rubber, is substantially U-shaped. The "U" formed by the shroud 90 surrounds the collector opening 54 and the heater opening 56 and in the probe 30 shown herein has its open end facing upward. Thus when the shroud 90 is positioned in contact with a surface to be sampled, with the heater opening 54 (and the lamp 60) in line with a target portion of the surface, the shroud 90 forms a channel to direct the flow of sampling air into the collector 36. Activation of the blower 66 causes air to be drawn into the open end of the U-shaped shroud 90, over the target portion of a sampling surface in contact with the shroud, and then into the collector opening 54. Provided the sampling surface is sufficiently flat that the flexible shroud 90 forms an air seal with the surface, essentially all of the air entering the collector 36 passes over the target portion heated by the lamp 60. The thickness of the shroud 90 and the width of its open end help determine the air speed over the target. Although high speeds provide scrubbing action which enhances removal of vapors from a target, it is also desirable to avoid excessive pressure drops by not restricting the flow area of prescribed values (e.g. a lower limit of flow area below 0.5 square inches has been determined to be suitable).

The flexible shroud 90, in addition to helping control the direction and speed of flow of air samples, helps protect sampling surfaces and front portions of the probe 30 from damage. The shroud may also include, or abut, a contact switch employed to initiate heating by the lamp 60 when the shroud 90 is pressed into contact with a sampling surface. A preferred contact switch is a membrane switch 92 interposed between the flexible shroud 90 and the front face 50 of the housing 40.

Figure 2:
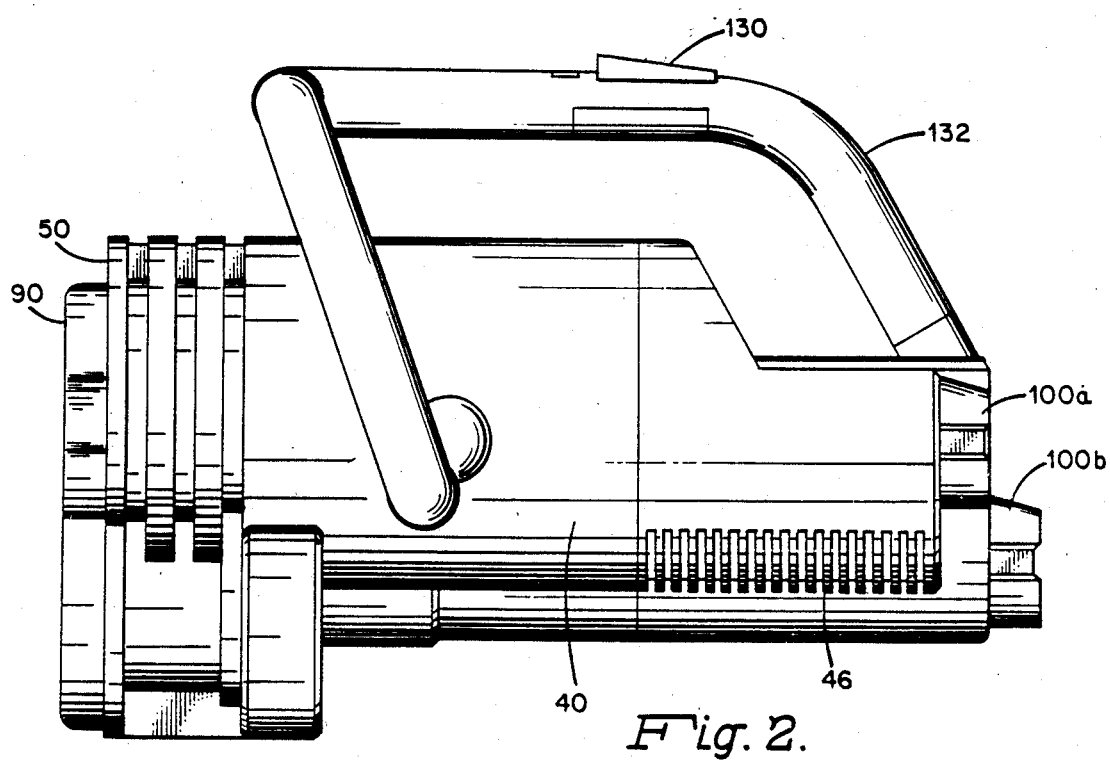
FIG. 2 is a side view of the vapor-sampling probe of FIG. 1.

To increase the vapor pressure of materials to be collected from a sampling surface the vapor-sampling probe 30 includes a heater, preferably an electrical lamp 60 such as a 24 volt (DC) 250 watt lamp. The lamp 60 is installed in a reflector 96 which is attached to a mounting ring 98 within the heater opening 56. As best shown in FIG. 5, the lamp 60 is wired to the main control board 80 which in turn is electrically connected to a rechargable battery 100. In the probe 30 shown by way of illustration herein, the battery 100 includes three series-connected battery packs 100a, 100b, and 100c (FIGS. 2, 4, 5). Each is removable from the rear of the probe 30 and may contain eight 1.2-volt rechargable nickel-cadmium batteries.

In order that the heat generated by the lamp not damage the sampling surface and also not decompose the vapors being collected, the probe 30 includes a pyrometer 104 with an infrared sensor for measuring the heat radiated by the target portion of the sampling surface and thus the temperature of the heated target. A preferred pyrometer is a model MINI T.E. available from the Williamson Company of Concord, Mass. The pyrometer 104 (FIG. 5) is mounted adjacent to the lamp 60 with its sensor oriented to receive radiation through an opening 108 in the wall of the heater chamber 96. As shown in FIG. 5, the pyrometer 104 is mounted at a selected angle from horizontal so that the field of view of its sensor on a target is essentially concentric with the field of the lamp 60. This permits the pyrometer 104 to accurately sense temperature of the target. If the sensed temperature of the surface attains a preset limit, such as 80° C. for fabrics or 100° C. for metals, then the main control board 80, which is electrically connected to the pyrometer 104 through a pyrometer control board 110, automatically shuts off the lamp 60.

Collection of vapors from a sampling surface may also be enhanced by the action of puffs of air directed at a target portion of the surface. For this purpose a puffer assembly 112 (FIG. 5) is included within the probe 30 and is connected by one or more flow lines 116 to puffer nozzles 120 (e.g., two nozzles) spaced about the lamp mounting ring 98. The nozzles 120 are aimed such that air jets emerging from the nozzles strike a target portion of a sampling surface opposite the lamp 60. A suitable puffer assembly 112 includes a solenoid 124 electrically connected to the main control board 80 and to an airpot 126. The airpot 126 has a cylinder containing a piston which, when driven by the solenoid 124, produces pulses of pressurized air which are directed along the flow lines 116 to the puffer nozzles 120. A low pressure-drop check valve (not shown) may be included in each flow line to prevent back flow into the puffer nozzle 120. During a typical sampling interval of about seven seconds the puffer assembly may, for example, deliver one puff of 20–25 cm$^3$ of air at about 10 psi (with total airflow being divided substantially evenly between or among all of the nozzles 120), or may be operated to deliver multiple puffs during the sampling interval. Puffing has been found to enhance efficiency of collection of vapors of substances such as cocaine.

Operation of the vapor-sampling probe 30 is triggered by a switch 130 in a hollow T-shaped handle 132 connected to the housing 40. The switch 130 is electrically connected to the main control board 80 by a wire 134, with the control board 80 in turn wired to the lamp 60, the motor 70, the pyrometer 104 and the puffer assembly 112. This arrangement, together with the light weight (less than 10 pounds) of the probe 30 and shape of the handle 132, readily permits the probe 30 to be aimed and operated utilizing two hands or just one. The switch 130, may be a simple on/off switch, or it may be a three-position switch with the first of two "on" positions activating the blower 66 and the second activating the lamp 60 and the puffer assembly 112 while the blower 66 remains in operation. The second "on" position need not be used when the vapor-sampling probe is employed to collect vapors in an open space—i.e., away from a surface—thereby conserving power in the battery 100 and extending the life of the lamp 60.

As was mentioned previously, the flexible shroud 90 on the front face 50 of the housing 40 may contain or abut a contact switch 92. With appropriate connections in the main control board 80, the contact switch 92 provides an alternative or second "on" position relative to operation of the lamp 60 and the puffer assembly 112. That is, the lamp 60 and the puffer assembly 112 may be activated upon either tripping of the switch 130 twice in succession, or a single trip of the switch 130 followed, or preceded, by activation of the switch 92 by pressure against the shroud 90. The double-trip sequence may be useful in collecting samples from surfaces which it is desired not to be touched by the shroud 90.

The main control board 80 is designed to permit the probe 30 to be configured or pre-programmed for any of a variety of sampling applications with minimum effort and without an operator having concerns for setting of switches, controls, etc. For this, the main control board 80 includes a microprocessor which is programmable by the manufacturer and which readily permits the varying of individual parameters such as the duration of sampling, the use of air puffs, the temperature of a target, and the length of time a target portion of a sampling surface is held at a prescribed temperature.

Analysis of the vapors collected by the vapor-sampling probe 30 of the invention requires that these vapors be transferred to a vapor detector. Although vapor analysis forms no part of the present invention, it should be noted that the vapor-sampling probe 30 includes features which facilitate the removal of collected vapors from its collector 36. As shown in FIGS. 1 and 3, the front face 50 of the probe housing 40 has a pair of alignment holes 142 and 144 outside the shroud 90. The holes 142 and 144 accommodate alignment pins on a vapor detector (not shown) to which the probe 30 may be attached during transfer of vapors. Removal of vapors from the collector 36 is preferably accomplished by electrically heating the metal windings of the collector coil 62 while flowing a carrier gas such as air under pressure through the coil 62 and into the vapor detector. For this, the vapor detector would be provided with a source of electrical power and a carrier gas supply, with electrical power being furnished to the coil 62 through electrical contacts 146 (one pair of the two sets of contacts 146 may be employed in regulating the power applied to the coil 62).

Figure 6:
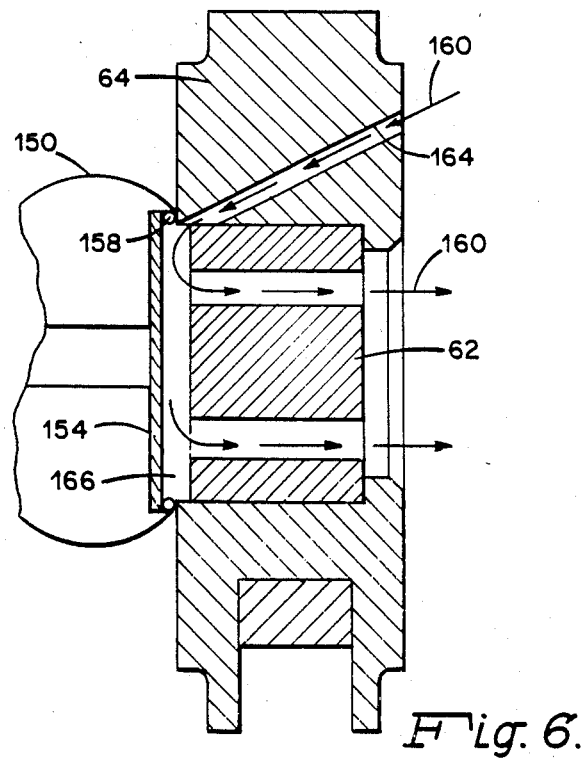
FIG. 6 is a cross-sectional side view, enlarged to show certain details, of a portion of the probe illustrated in FIG. 5.

In order that carrier gases both enter and exit the coil 62 through the front end of the probe 30 during desorption of vapors, a back seal 150 is provided in the collection chamber 38 of the probe 30 behind the coil 62. The seal 150 includes a closure plate 154 which during operation of the probe 30 in a collection mode is spaced from the coil 62 so that it does not appreciably restrict flow through the probe 30 or add to pressure losses. During collection, gases exiting the coil 62 readily flow around the seal 150, as illustrated by the arrows 156 in FIG. 5. To desorb a sample, the probe 30 is first interfaced to a detector (not shown) by coupling the front face 50 of the probe to the detector and in so doing displacing the coil 62 and its housing 64 rearward to seal against an O-ring 158 and in turn against the closure plate 154. As indicated by the arrows 160 in FIG. 6, carrier gas from a source within the detector (not shown) then is directed through a desorption gas passage 164, into the space 166 between the closure plate 154 and the coil 62, and across the surfaces of the coil 62, on which vapors have previously been trapped. With the coil 62 heated by an electrical current, the flowing carrier gas strips vapors from the coil surfaces and carries them out the front of the coil 62 and into the detector for analysis. After the desorption cycle is complete, the probe 30 is placed in a rest position on, or is removed from, the detector, allowing the coil 62 and its housing 64 to spring back to their normal collection position.

Other features may be included in the vapor-sampling probe 30 to enhance its utility. To allow recharging of the battery 100 and also permit operation of the probe on external power, one of the battery packs such as pack 100b may include a receptacle 168 for an electrical plug. Also, a battery indicator light may be provided—for example, near the handle switch 130.

A typical sample acquisition by the vapor-sampling probe 30 is initiated by aiming the lamp 60 at a target portion of a surface such as at a mark or spot visible on a package suspected of containing cocaine or heroin or at a selected area of a coat of a person passing through a checkpoint. The shape of the probe 30 illustrated herein, wherein the lamp 60 is mounted in the center of the main barrel-like portion of the housing 40, facilitates accurate aiming of the probe to place the lamp 60 directly over the spot or target to be sampled. With the flexible shroud 90 pushed into contact with the sampling surface so as to activate the membrane switch 92, depression of the handle switch 130 turns on the blower 66, the lamp 60, and the puffer assembly 112 (if present). Vapors are dislodged from the target by heat from the lamp 60, the action of air jets from the puffer nozzles 120, and airflow induced by the sucking action of the blower 66. Air is drawn over the target and is swept with vapors into the collector 36 at a high flow rate such as about two liters/second. A substantial fraction of the vapors are trapped on the coating of the collector coil 62 for subsequent desorption and analysis, with the remaining flow exhausted through the air vents 46. A typical sample acquisition time is about seven seconds and the main control board may be programmed to limit the air puffing and/or heating to a specified maximum duration such as seven seconds. Repeated pushing of the handle switch 130 may, of course, be employed to provide a second or third cycle for surfaces from which sample acquisition is known to be difficult, or for which higher concentrations of trapped vapors are desired for analysis. Also, the duration of heating may be subject to shortening by automatic shutdown of the lamp 60 if the temperature of the target exceeds predetermined levels.

What is claimed is:

1. A hand-operable sampling probe for collecting vapors comprising:
   a housing including a front face having a collector opening in communication with a collector chamber within the housing, said collector chamber shaped to hold therein a gas-permeable vapor collector;
   heater means for directing heat outward from said front face;
   said front face having a heater opening at a position spaced from said collector opening, and said heater means including a lamp mounted in said heater opening;
   blower means within said housing for directing a gas sample through the collector opening and through said gas-permeable collector with said collector held in said collector chamber, and for exhausting gases from the housing;
   a power supply for furnishing electrical power to said heater means and said blower means;
   a handle attached to, and extending outward from, said housing; and
   a shroud attached to said housing and extending forward of said front face, said shroud and front face operable, when the shroud is positioned in contact with, or near, a sampling surface, to control the direction of gas flow over the surface and into said collection chamber.

2. A sampling probe as in claim 1 wherein said shroud includes a rear surface attached to said front face and a front surface, said shroud being formed in a shape such that, when said front surface is positioned in contact with a sampling surface and said blower means is activated, essentially all the air directed through the collector is first drawn over a target portion of the sampling surface opposite said heater means.

3. A sampling probe as in claim 2 wherein said shroud is substantially U-shaped and defines a channel aligned with said heater opening and said collector opening, with said collector opening being closer to the closed end of said U than is said heater opening.

4. A sampling probe as in claim 3 wherein the thickness of said shroud and the open end of said U are selected to provide, when said front surface of the shroud is positioned in contact with a surface to be sampled, a flow area for air of at least about 0.5 square inches.

5. A sampling probe as in claim 1 including a pyrometer for sensing the temperature of a target portion of said sampling surface during heating of said target portion by said lamp, said pyrometer having a field of view generally concentric with the field of view of the lamp on said target portion.

6. A hand-operable sampling probe for collecting vapors comprising:
   a housing including a front face having a collector opening in communication with a collector chamber within the housing, said collector chamber shaped to hold therein a gas-permeable vapor collector;
   heater means for directing heat outward from said front face;
   blower means within said housing for directing a gas sample through the collector opening and through said gas-permeable collector with said collector held in said collector chamber, and for exhausting gases from the housing;
   a power supply for furnishing electrical power to said heater means and said blower means;
   a handle attached to, and extending outward from, said housing;
   a shroud attached to said housing and extending outward from said front face;
   a first switch in said handle;
   a second switch responsive to pressure on the front surface of said shroud; and
   a controller connected to said power supply, to said switches, and to said heater means, said controller operable to start said heater means only upon activation of both said switches.

7. A sampling probe as in claim 6 including puffer means connected to said controller for directing puffs of air from said front face toward a sampling surface, said puffer means operable only upon activation of both said switches.

8. A hand-operable sampling probe for collecting vapors comprising:
   a housing including a front face having a collector opening in communication with a collector chamber within the housing, said collector chamber shaped to hold therein a gas-permeable vapor collector;
   heater means for directing heat outward from said front face;
   blower means within said housing for directing a gas sample through the collector opening and through said gas-permeable collector with said collector held in said collector chamber, and for exhausting gases from the housing;
   a power supply for furnishing electrical power to said heater means and said blower means;
   puffer means for directing puffs of air from said front face towards a target portion of a sampling surface;
   a handle attached to, and extending outward from, said housing; and
   a shroud attached to said housing and extending outward from said front face.

9. A hand-operable sampling probe for collecting vapors comprising:
- a housing including a front face having a collector opening in communication with a collector chamber within the housing, said collector chamber shaped to hold therein a gas-permeable vapor collector;
- heater means for directing heat outward from said front face;
- blower means within said housing for directing a gas sample through the collector opening and through said gas-permeable collector with said collector held in said collector chamber, and for exhausting gases from the housing;
- means for sensing the temperature of a target portion of a sampling surface during heating of said target portion by said heater means;
- a power supply for furnishing electrical power to said heater means and said blower means; and
- a handle attached to, and extending outward from, said housing.

10. A sampling probe as in claim 9 wherein said power supply includes a rechargeable battery, and said probe further includes a controller electrically connected to said battery and operable to regulate operation of said heater means and said blower means.

11. A hand-operable sampling probe for collecting vapors comprising:
- a housing including a front face having a collector opening in communication with a collector chamber within the housing and a lamp opening spaced from said collector opening, said collector chamber shaped to hold therein a gas-permeable vapor collector;
- heater means for directing heat outward from said front face;
- blower means within said housing for directing a gas sample through the collector opening and through said gas-permeable collector with said collector held in said collector chamber, and for exhausting gases from the housing;
- a power supply for furnishing electrical power to said heater means and said blower means;
- a handle attached to, and extending outward from, said housing;
- a shroud attached to said housing and extending forward of said front face, said shroud and front face operable, when the shroud is positioned in contact with, or near, a sampling surface, to control the direction of gas flow over the surface and into said collection chamber;
- a mounting ring within said lamp opening; and
- a lamp attached to said mounting ring.

12. A sampling probe as in claim 11 including puffer means for directing puffs of air at a target portion of said sampling surface, said puffer means comprising, within said housing, an airpot, a solenoid connected to said airpot, means for pulsing said solenoid to produce said puffs of air, an air nozzle within said mounting ring, and an airflow line connected between said nozzle and the outlet of said airpot.

13. A hand-operable sampling probe for collecting vapors comprising:
- a housing including a front face having a collector opening in communication with a collector chamber within the housing, said collector chamber shaped to hold therein a gas-permeable vapor collector;
- heater means for directing heat outward from said front face;
- blower means within said housing for directing a gas sample through the collector opening and through said gas-permeable collector with said collector held in said collector chamber, and for exhausting gases from the housing;
- a power supply for furnishing electrical power to said heater means and said blower means;
- a handle attached to, and extending outward from, said housing;
- a shroud attached to said housing and extending outward from said front face, said shroud being formed of an elastomeric material; and
- a switch responsive to pressure on the front surface of said shroud for activation of said heater means.

14. A sampling probe for collecting vapors comprising:
- a housing defining a collection chamber near its front end and further defining at least one exhaust port;
- a collector removably mounted in said collection chamber and operable to trap vapors from an air sample passed therethrough;
- blower means within said housing for drawing an air sample through said collector and exhausting air through said exhaust port;
- heater means for directing heat outward from said front end of the housing so as to heat a target portion of a surface upon operation of said heater means with said front end positioned near said target portion;
- a power supply for furnishing electrical power to said heater means and said blower means;
- means for sensing the temperature of said target portion of said sampling surface; and
- a controller connected to said temperature sensor and to said heater means and operable to interrupt operation of said heater means when said temperature sensor senses a temperature of a preselected level.

15. A sampling probe as in claim 14 including a shroud attached to, and extending forward of, the front end of said housing, the thickness of said shroud regulating the minimum spacing between said front end of the housing and a sampling surface.

16. A sampling probe as in claim 15 wherein said shroud is flexible and shaped to define a flow channel such that, upon the placement of the forward surface of the shroud in contact with a sampling surface with said heater means aligned with a target portion of said sampling surface, activation of said blower means causes air to be drawn from outside the shroud into said flow channel, then over said target portion and then through said collector.

17. A sampling probe as in claim 16 wherein said shroud is substantially U-shaped with said collector being closer to the closed end of said U than is said heater means.

18. A sampling probe as in claim 14 including puffer means for directing puffs of air to impact a target portion of a sampling surface upon operation of said puffer means with said heater means positioned near said target portion.

19. A sampling probe for collecting vapors comprising:
- a housing having a front face, said front face having first and second openings spaced from each other and defining, respectively, a collector chamber and a heater chamber, said housing further defining an exhaust port;

a collector mounted in said collector chamber and operable to trap vapors upon passage of an air sample therethrough;

a blower within said housing for drawing an air sample through said collector and exhausting air through said exhaust port;

a heater mounted within said heater chamber for directing radiant energy outward from said heater chamber, said heater, upon being activated near and in alignment with a target portion of a sampling surface, operable to heat said target portion;

a handle connected to said housing;

means for supplying electrical power to said blower and said heater; and switch means at least partially within said handle for activating and deactivating said heater and said blower, said switch means having a first setting in accordance with which said blower is activated and a second setting in accordance with which said blower and said heater are both activated.

20. A sampling probe as in claim 19 wherein said collector is movable within said collection chamber between a vapor collection position and a vapor desorption position, and said probe includes, within said collection chamber, first passage means for permitting gases to be drawn into said collection chamber, through said collector, and then out through said exhaust port while said collector is in said vapor collection position and second passage means for permitting gases to be directed into said collection chamber, through said collector, and out of the front of said collection chamber while said collector is in said vapor desorption position, and further including sealing means for blocking flow through said first passage means while said collector is in said vapor desorption position.

21. A sampling probe as in claim 19 including a flexible shroud attached to, and extending forward of, said front face, said shroud having a shape such that when the blower is activated with the shroud positioned near or in contact with a sampling surface, an air sample is drawn over said target portion and then into said collector.

22. A sampling probe as in claim 21 wherein said switch means includes a first switch in said handle and a second switch responsive to pressure on a front surface of said shroud, and the second setting of said switch means includes the tripping of both said switches.

23. A sampling probe as in claim 19 including means for sensing the temperature of said target portion of a sampling surface and control means responsive to said temperature sensing means for deactivating said heater upon the sensing of a temperature of said target portion equal to said prescribed temperature.

24. A sampling probe as in claim 19 wherein said means for supplying electrical power comprises a battery mounted within said housing.

* * * * *